United States Patent [19]
Van Veen et al.

[11] Patent Number: 5,263,488
[45] Date of Patent: Nov. 23, 1993

[54] METHOD AND APPARATUS FOR LOCALIZATION OF INTRACEREBRAL SOURCES OF ELECTRICAL ACTIVITY

[75] Inventors: Barry D. Van Veen, McFarland; Jon Joseph; Kurt E. Hecox, both of Madison, all of Wis.

[73] Assignee: Nicolet Instrument Corporation, Madison, Wis.

[21] Appl. No.: 957,190

[22] Filed: Oct. 5, 1992

[51] Int. Cl.$^5$ .................................. A61B 5/0476
[52] U.S. Cl. ...................................... 128/731
[58] Field of Search ........................ 128/731, 732

[56] References Cited

U.S. PATENT DOCUMENTS

| | | | |
|---|---|---|---|
| 4,736,751 | 4/1988 | Gevins et al. | 128/732 |
| 4,949,725 | 8/1990 | Raviv et al. | 128/731 |
| 5,037,376 | 8/1991 | Richmond et al. | 128/897 |

OTHER PUBLICATIONS

B. Van Veen, "Minimum Variance Beamforming," in Adaptive Radar Detection and Estimation, S. Haykin and A. Steinhardt, eds., John Wiley and Sons, Ch. 4, 1992, pp. 161–236.

Van Veen, et al., "Multiple Window Based Minimum Variance Spectrum Estimation for Multidimensional Random Fields," IEEE Transactions on Signal Processing, vol. 40, No. 3, Mar. 1992, pp. 578–589.

D. W. Marquardt, "An Algorithm For Lease-Squares Estimation of Nonlinear Parameters," J. Soc. Indust. Appl. Math. vol. 11, No. 2, Jun. 1963, pp. 431–441.

M. R. Schneider, "A Multistage Process for Computing Virtual Dipolar Sources of EEG Discharges from Surface Information," IEEE Transactions on Biomedical Engineering, vol. BME-19, No. 1, Jan. 1972, pp. 1–12.

C. J. Henderson, et al., "The Localization of Equivalent Dipoles of EEG Sources by the Application of Electrical Field Theory," Electroencephalography and Clinical Neurophysiology, 1975, vol. 39, pp. 117–130.

R. D. Sidman, et al., "A Method for Localization of Sources of Human Cerebral Potentials Evoked by Sensory Stimuli," Sensory Processes, vol. 2, 1978, pp. 116–129.

R. N. Kavanagh, et al., "Evaluation of Methods for Three Dimensional Localization of Electrical Sources in the Human Brain," IEEE Transactions on Biomedical Engineering, vol. BME-25, No. 5, Sep. 1978, pp. 421–429.

T. M. Darcey, et al., "Methods for the Localization of Electrical Sources in the Human Brain," Prog. Brain Res., vol. 54, 1980, pp. 128–134.

M. Scherg, et al., "A New Interpretation of the Generators for BAEP Waves I–V: Results of a Spatio-Temporal Dipole Model," Electroencephalography and Clinical Neurophysiology, 1985, vol. 62, pp. 290–299.

(List continued on next page.)

Primary Examiner—William E. Kamm
Assistant Examiner—Scott M. Getzow
Attorney, Agent, or Firm—Foley & Lardner

[57] ABSTRACT

Signals from plural electrodes placed at known positions on the head of an individual are digitized and processed in a computer processor which includes a bank of spatial filters. The filters are designed to meet a linearly constrained minimum variance criterion so that they each substantially pass signal energy from a location within the brain known with respect to the electrodes while rejecting signal energy from other locations within the brain. The outputs of the filters can be used to estimate the signal power at each of the locations in the brain, or the dipole moment at each location, and this information can be displayed on a display device to provide a map of source activity within the brain. The spatial filters do not require prior knowledge of the number of sources, and the number of discrete sources can be identified as well as the location, power, and dipole moment of the sources. This information can be used when a stimulus is applied to the individual to determine the regions of the brain which respond to the stimulus, or to localize neural activity in the brain to identify the location of pathology within the brain.

36 Claims, 4 Drawing Sheets

OTHER PUBLICATIONS

M. Scherg, et al., "Evoked Dipole Source Potentials of the Human Auditory Cortex," Electroencephalography and Clinical Neurophysiology, 1986, vol. 65, pp. 344–360.

D. H. Fender, "Source Localization of Brain Electrical Activity," in Methods of Analysis of Brain Electrical and Magnetic Signals, EEG Handbook, revised series, vol. D (book), A. S. Gevins & A. Redmond, Eds., Elsevier Science Publishers B.V. 1987, Chapter 13, pp. 355–403.

A. Van Oosterom, "History and Evolution of Methods for Solving the Inverse Problems," Journal of Clinical Neurophysiology, vol. 8, No. 4, 1991, pp. 371–380.

D. H. Feder, "Models of the Human Brain and the Surrounding Media: Their Influence on the Reliability of Source Localization," Journal of Clinical Neurophysiology, vol. 8, No. 4, 1991, pp. 381–390.

METHOD AND APPARATUS FOR LOCALIZATION OF INTRACEREBRAL SOURCES OF ELECTRICAL ACTIVITY

FIELD OF THE INVENTION

This invention pertains generally to the field of electroencephalographic measurement apparatus and techniques and particularly to the non-invasive determination of the location of intracerebral sources of electrical activity.

BACKGROUND OF THE INVENTION

Millions of individuals worldwide suffer from various forms of seizure disorders. In most cases, these individuals can be treated with standard regimes of medications (anti-convulsants) which offer acceptable results. Less commonly, an individual may have an "intractable" form of epilepsy in which most reasonable forms of medical therapy have failed to provide adequate relief. Surgical excision of the portion of the cerebrum responsible for the abnormal electrical activity is one alternative to medical therapy in such intractable cases. The popularity of the surgical treatment of epilepsy has increased substantially since the release of a National Health Institute report supporting the efficacy of surgical intervention in appropriately selected cases. One of the key elements in selecting patients is an understanding of the number and anatomic location of sites of abnormal electrical activity. To the extent that there are multiple or widely distributed abnormal sites, surgical intervention is less likely to succeed. Thus, precise knowledge of the number and location of intracerebral sources of seizure activity is critical to successful surgical intervention.

There are a number of other surgical procedures, e.g., involving removal of cerebral tumors, where determining the location of the tissue of origin of activity or control (for example, hand, face or foot movement) is important in guiding the surgeon's efforts. Similarly, the value of evoked potential studies would be enhanced by a more detailed knowledge of the anatomic origin of the multiple components of the evoked potential (EP) waveform. While numerous methods have been proposed to determine the location of EP components, none has succeeded in handling the analysis of multiple simultaneous sources.

A variety of assessment tools are used by neurologists to assess the functional status of different regions of the brain, with the most common being the electroencephalogram (EEG). From the view point of the neurologist, it would be desirable to be able to determine the location of sources of electrical activity within the brain using electrical field potential measurements made at the scalp. Multiple sensors placed at different locations on the scalp may be employed to sample the spatial distribution of the electric potential a the scalp surface. To allow sources within the brain to be located, it is necessary to use a model that relates the underlying neural activity to the distribution of potential as measured by the surface sensors. Such models rely on the solution of the "forward" problem. The forward problem may be simply described as calculation of the scalp potential due to a known neural source in a known location. The solution to the forward problem requires assumption of a model for the geometry and physiological properties of the head.

The most commonly used model of the head is a three shell spherical model (scalp, skull, brain parenchyma). More sophisticated models derived from magnetic resonance imaging (MRI) or other imaging of the head offer increased realism at the expense of considerable additional testing and computation. Calculation of the intracranial source distribution responsible for an observed scalp potential field is called the "inverse" problem.

Electrical activity detected from scalp electrodes does not generally reflect the contribution of a single neuron, but, more typically, hundreds or thousands of neurons firing nearly synchronously. The geometric arrangement of these neurons can profoundly effect the "net equivalent" dipole detected from a distant recording site. In the extreme, complete cancellation of electrical activity can occur with certain cellular geometries, resulting in a zero mean moment, as measured from a distance. The inability to detect the electrical response from certain classes of geometric arrangements is an intrinsic weakness of most signal processing algorithms. In contrast, the present invention is dependent upon both first order (mean) and second order (variance) statistics. Thus, zero mean equivalent dipoles can be detected as long as there is a non-zero variance component. Control of the contribution of first versus second order statistics to the output of the localization algorithm can be manipulated by changes in stimulus parameters or by changes of algorithm terms.

Depending on the specific source (e.g. spike, visual evoked potential, etc.), the equivalent dipole will likely shift over time. By performing the localization algorithm at any instant in time and repeatedly applying the algorithm over time, a representation of source spatial movement with time can also be generated.

SUMMARY OF THE INVENTION

In accordance with the present invention, the distribution of neural power is estimated as a function of location within the brain using a bank of spatial filters. The spatial filter responses are designed in a data adaptive manner using the linearly constrained minimum variance (LCMV) criterion. In contrast to commonly used least squares fitting techniques, the present invention does not require knowledge of the number of sources present. It is also applicable to complex source distributions such as dipole sheets. Zero mean equivalent dipole sources can be detected as long as there is a non-zero variance component.

The apparatus of the invention receives electrical signals from plural electrodes which are distributed around the head of an individual at known locations, and converts the electrical signals to digital data signals in a digitizer. The analog signal is preferably amplified and filtered before being converted to the digital data signal. The digital signal is operated on in a processing unit to carry out spatial filtering on the data signal. The spatial filters are narrow band filters which substantially pass the signal energy from a location within the brain which is known with respect to the electrode positions and reject signal energy from other locations. Typically, a large number of filters will be provided to pass signal energy from a large number of locations within the brain. These locations may comprise, for example, the points of a fairly dense three dimensional rectangular grid which extends through the volume of the brain. Each of the filters meets a linearly constrained minimum variance criterion. The processing unit may estimate the signal power in the output of each of the filters, which corresponds to the power at each of the locations, and may estimate the dipole moment in the output of each filter which corresponds to the dipole moment at each of the locations. The filters can provide information on locations throughout the entire volume of the brain, or at only a specified portion of the brain. By constructing the filters in this manner, it is not necessary to have prior knowledge of the number of discrete sources which are to be located since such information is not necessary to construct the spatial filters. Consequently, the invention provides information to the user which can identify the number, location, relative power, and dipole moment orientation of several discrete sources within the brain. Moreover, this information can be collected over a period of time, which allows the changes in these characteristics of the sources to be tracked over time. This is particularly valuable during evoked potential studies where a stimulus is provided by a stimulator to the individual, resulting in transient electrical activity within the brain in response to the stimulus.

Further objects, features and advantages of the invention will be apparent from the following detailed description when taken in conjunction with the accompanying drawings.

DETAILED DESCRIPTION OF THE INVENTION

Figure 1:
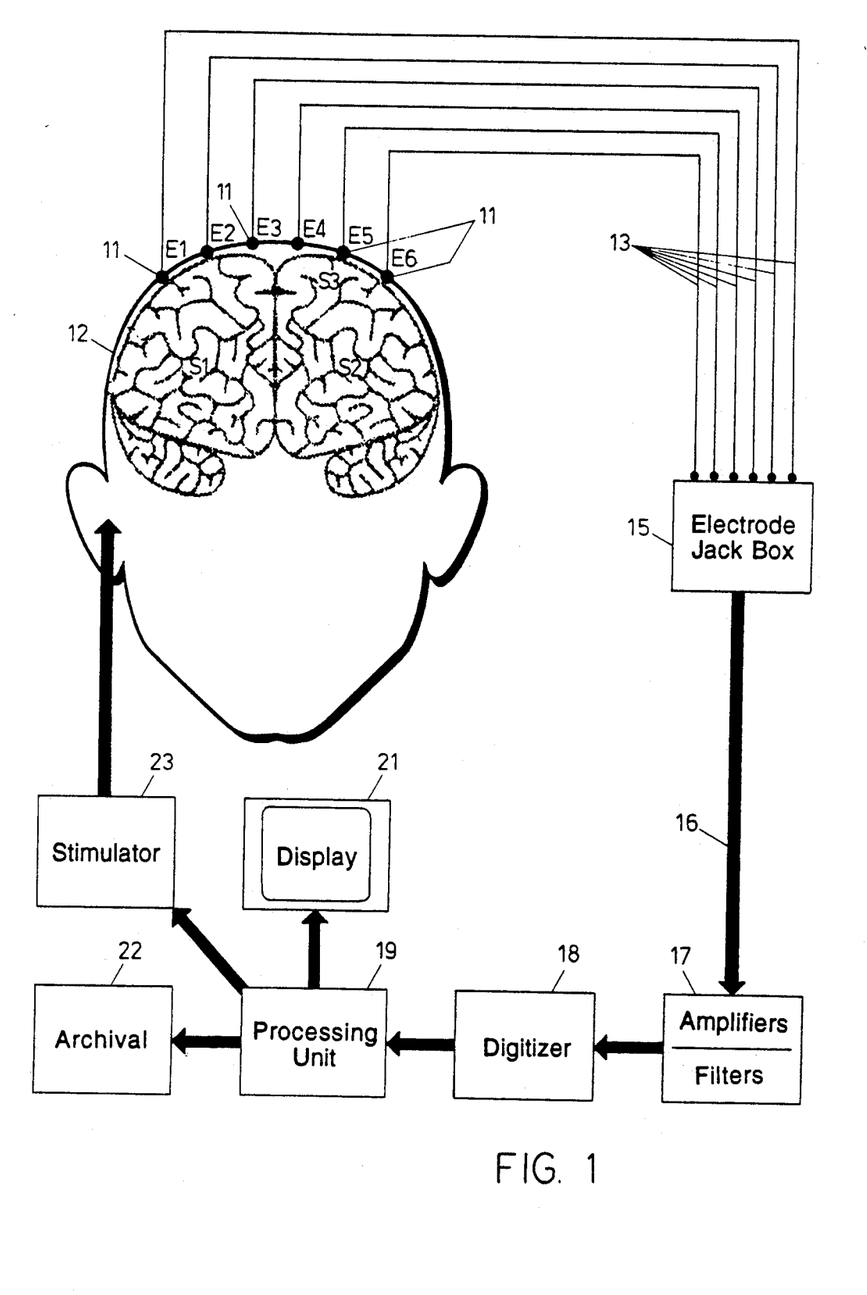
FIG. 1 is a schematic diagram of the apparatus of the invention for determining the location of intracerebral sources of electrical activity utilizing EEG electrode data.

A general block diagram of an apparatus in accordance with the invention for determining the location of intracerebral sources of electrical activity is shown generally in FIG. 1. The apparatus receives data from a plurality of electrodes 11 which have been attached to the scalp of the head of an individual (shown schematically at 12). A series of six electrodes 11, labeled E1-E6, are shown for illustrative purposes, but, as described below, typically many more electrodes will be utilized. An electrical reference may be provided in a conventional fashion. The placement of the reference electrode is generally not crucial in the present invention. It is understood that magnetoencephalographic sensors may be used in the present invention in appropriate cases and may be considered "electrodes" as used herein. The present invention determines the location within the head 12 at which sources of electrical activity originate. Various sources are illustratively shown in the schematic drawing of FIG. 1 at S1, S2 and S3. In general, the shape and size of the head 12 of the individual will be determined before measurements are taken in accordance with the present invention. The electrodes E1-E6, etc., are attached to the scalp at locations which are recorded and which are located with regard to coordinates referenced to the individual's head 12 so that the position of the sources S1-S3 can be determined from information gathered from the electrodes, the position of which is known, recorded, and available for correlation with regard to the data that is developed based on the signals from the electrodes. The electrode signals are transmitted via lines 13 to an electrode jack box 15, in accordance with standard EEG electrode practice, and the multiple signals from the electrode jack box are connected through a transmission cable 16 to a signal condition unit of amplifier and filters 17. The analog signals from the signal conditioning unit 17 are provided to a digitizer 18 which samples the analog input data and provides a series of digital output data to a computer processing unit 19, which may be a general purpose computer programmed in accordance with the present invention. Based on the electrode signal information and the positions of the electrodes, the signal processing unit 19 generates data indicative of one or more signal locations S1-S3, etc., and this data is provided to a display device 21, e.g., a video display, and may also be transmitted to archival storage 22, such as a floppy disk, hard disk, or other long term data storage device. The computer processing unit may, in the case of evoked potential studies, control a stimulator 23 to produce a signal which stimulates a sensory system at or before electrical signals are obtained from the electrodes to result in electrical activity within the head 12 of the individual being tested. In the case of evoked potential studies, data acquisition and stimulus delivery are temporally synchronized by the processing unit. Various types of stimulators may be used which are well known, e.g., to stimulate hearing, sight or touch.

In the present invention, the determination of the intracranial source distribution responsible for the scalp potential field observed by the electrodes E1-E6, which may be called the "inverse" problem, is carried out by estimating the distribution of neural power as a function of location within the brain using a bank of spatial filters. The spatial filter responses are carried out in an adaptive manner using the linear constrained minimum variance (LCMV) criterion, which does not require a priori knowledge of the number of sources that are present. Thus, the present invention can determine the location of a single source within the brain, or of multiple sources, without knowing the number of sources at any particular time. In general, it is observed that the number and location of sources of electrical activity change in the brain over time, particularly with changes in the types of brain activity or the stimuli applied to the brain. The following discussion explains the analytical basis for the present invention. In the mathematical notation used, boldface lower and upper case symbols denote vectors and matrices, respectively, and a $T$ represents a matrix or vector transpose.

The present invention is based on source and head models that relate the underlying neural activity to the distribution of potential measured by surface electrodes. An individual neuron is reasonably modeled as a current dipole or sum of current dipoles. The medium is linear, so the potential at the scalp is the superposition of the potentials from many active neurons. Furthermore, the firing of individual neurons is governed by a probabilistic law, so the scalp activity is approximated by a random process. Observations of this random process at the electrodes are used to infer the properties of the underlying neural activity. Specifically, the first and second order statistics of the underlying neural activity as a function of location, the mean dipole moment and dipole covariance, are of interest.

Let x be an N by 1 vector composed of the potentials measured at the N electrode sites at a given instant in time. The potential due to a single dipole source with location represented by the vector q is expressed as $x = H(q)m(q)$ where the elements of the 3 by 1 vector $m(q)$ are the x,y, and z components of the dipole moment at the given instant in time and the columns of the N by 3 matrix $H(q)$ represent solutions to the forward problem. That is, the first column of $H(q)$ is the potential at the electrodes due to a dipole source at location q having unity moment in the x direction and zero moment in y and z directions. Similarly, the second and third columns represent the potential due to sources with unity moment in y and z directions, respectively.

Define a differential volume element dq centered on location $q \in \Omega$ having where $\Omega$ is the volume of cerebral tissue in which the electrical activity originates. Let $m(dq)$ be a three by one random vector on the set dq whose statistical properties characterize the net moment at q associated with the local collection of neurons. Let $v(dq)$ be the mean value of $m(dq)$ and define $s(dq) = m(dq) - v(dq)$. We assume $s(dq)$ is an orthogonal process on $\Omega$. Hence, the aggregate measured scalp potential at the electrodes may be expressed as $$x = \int_\Omega H(q)v(dq) + \int_\Omega H(q)s(dq) + n \qquad (1)$$

where n is noise due to signals originating outside the volume of cerebral tissue. The noise n is assumed to be uncorrelated with the signal which is due to neural activity and is further assumed to have zero mean. Hence, the mean $m_x$ and covariance $R_x$ of the measured potentials is $$m_x = \int_\Omega H(q)v(dq) \qquad (2a)$$

$$R_x = \int_\Omega H(q)S(q)H^T(q)dq + R_n \qquad (2b)$$

using equation (1) and the orthogonality properties of $s(dq)$. $R_n$ is the noise covariance matrix. The 3 by 3 matrix $S(q)$ is termed the moment power density and describes the moment covariance at q. The diagonal elements of $s(q)$ represent the variance of the x, y, and z components of the local moment density. Thus, the net moment mean g, and covariance M, in a local small volume Q is $$g(Q) = \int_Q v(dq) \qquad (3a)$$

$$M(Q) = \int_Q S(q)dq \qquad (3b)$$

The total power, P, in a volume Q is $$P(Q) = tr M(Q) + g^T(Q)g(Q). \qquad (3c)$$

As used herein, trA denotes the trace of a matrix A.

The localization problem is one of estimating the power in small volume elements as a function of location within $\Omega$. The integrated (over Q) moment power density matrix $S(q)$ and moment mean $g(Q)$ provides additional information about the characteristics of the local dipole moment.

Consider passing the data x through a bank of "narrow band" spatial filters where each filter passes energy originating from a specified location within the brain and attenuates energy from other locations. Hence, the power at each filter output is the moment power in the volume corresponding to the filter pass band. Define the spatial filter for the volume element $Q_o$ centered on location $q_o$ as the N by 3 matrix $W(q_o)$ and let the filter output y be the inner product of $w(q_o)$ and x: $y = W^T(q_o)x$. Here y is 3 by 1. The mean and covariance of y is $$m_y = W^T(q_o)m_x \qquad (4a)$$

$$R_y = W^T(q_o)R_x W(q_o). \qquad (4b)$$

Substitution of equations (2a) and (2b) in equations (4a) and (4b) yields $$m_y = \int_{q \in Q} W^T(q_o)H(q)v(dq) + \int_{\substack{q \notin Q \\ q \in \Omega}} W^T(q_o)H(q)v(dq) \qquad (5a)$$

$$R_y = \int_{q \in Q} W^T(q_o)H(q)S(q)H^T(q)W(q_o)dq + \int_{\substack{q \notin Q \\ q \in \Omega}} W^T(q_o)H(q)S(q)H^T(q)W(q_o)dq + W^T(q_o)R_n W(q_o) \qquad (5b)$$

Now suppose the spatial filter satisfies $$W^T(q_o)H(q) = \begin{cases} I & \text{if } q \in Q_o \\ 0 & \text{if } q \notin Q_o, \ q \in \Omega \end{cases} \qquad (6)$$

Ignoring the noise term in (5b) and substituting (6) gives $$m_y = g(Q_o) \qquad (7a)$$

$$R_y = M(Q_o). \qquad (7b)$$

Thus, $P(Q_o) = trR_y + m_y^T m_y$. That is, the filter output power is the net moment power in the volume $Q_o$.

Temporarily assume that $v(dq) = 0$ and concentrate on the covariance terms. Equation (6) describes the spatial analog of an ideal narrow band filter. In practice, zero response for $q \notin Q_o$ can only be approximated so the second integral in (5b) will generally be non-zero. This difference is minimized if $W^T(q_o)H(q)$ is smallest at values $q \notin Q_o$ where $S(q)$ is non-zero. Also note that the noise term in (5b) biases $R_y$ away from the true moment covariance $M(Q_o)$. These errors are minimized by choosing $W(q_o)$ according to a linearly constrained minimum variance (LCMV) criterion:

$$\min_{W(q_o)} trR_y \text{ subject to } W^T(q_o)H(q_o) = I. \qquad (8)$$

Minimization of power minimizes the contributions of noise and covariance components generated outside the region of interest, $q \notin Q_o$, while the constraint ensures that the energy of interest in $Q_o$ is passed with unit gain. The solution to (8) is obtained as $$W(q_o) = R_x^{-1} H(q_o) (H^T(q_o) R_x^{-1} H(q_o))^{-1}. \quad (9)$$

Let ^ over a symbol represent a quantity estimated using $W(q_o)$. Substation of (9) gives $$\hat{M}(Q_o) = (H^T(q_o) R_x^{-1} H(q_o))^{-1} \quad (10a)$$

$$\hat{P}(Q_o) = tr\{(H^T(q_o) R_x^{-1} H(q_o))^{-1}\}. \quad (10b)$$

The net moment power is estimated as a function of location by evaluating (10) on a dense grid of locations (e.g., a three dimensional rectangular grid of location points) over the volume of the brain, $\Omega$.

If the moment is not zero mean ($v(dq) \neq 0$), then the filter weights should be chosen to attenuate both covariance and mean components generated outside the region of interest, $q \notin Q_o$, in addition to noise. This is accomplished by solving $$\min_{W(q_0)} tr W^T(q_0)[R_x + mm^T] W(q_0) \text{ subject to } W^T(q_0) H(q_0) = I \quad (11)$$

where m is the component of $m_x$ that lies in the space orthogonal to that spanned by the columns of $H(q_o)$. That is, $m = [I - H(q_o)(H^T(q_oH(q_o))^{-1} H^T(q_o)]m_x$. It can be shown that if m is replaced by $m_x$ in (ii), then the filter will significantly attenuate all non-zero mean components in the data, including the component of interest. Use of m ensures that the filter does not attenuate the mean component at $q_o$, but does ensure that the filter will attenuate the mean components represented in m. The solution to (11) is $$W(q_o) = (R_x + mm^T)^{-1} H(q_o)\{H^T \cdot (q_o(R_x + mm^T)^{-1} H(q_o)\}^{-1}. \quad (12)$$

The estimated mean vector, covariance matrix, and power are obtained using (12) in $$\hat{g}(Q_o) = W^T(q_o) m_x \quad (13a)$$

$$\hat{M}(Q_o) = W^T(q_o R_X W(q_o) \quad (13b)$$

and $$\hat{P}(Q_o) = tr\{W^T(q_o)(R_x + m_x m_x^T) W(q_o)\}. \text{tm (13c)}$$

The net moment power is estimated as a function of location by evaluating equations (10b) or (13c) on a dense grid of locations over the volume of the brain, $\Omega$. Note that the LCMV method does not require knowledge of the number of active sources or make assumptions concerning source geometry.

One mechanism for enhancing the variance component is to randomly or semi-randomly change stimulus parameter values. For example, as the frequency of an auditory stimulus is changed, the specific cells activiated by the stimulus also change (i.e., there is a tonotopic representation of frequency in brain anatomy). Changing stimulus frequency would therefore, produce variability in the physical properties of the equivalent dipole, which is then reflected as increased variance. There are many parameters which can be changed, such as frequency, intensity, contrast, duration, complexity, etc., and selection of the magnitude of variation and optimal parameters for variation depends on the specific targeted dipole.

An alternate method for using the LCMV filters to estimate the dipole moment mean $g(Q_o)$ is obtained by assuming that all sources have a covariance component. This assumption is particularly appropriate when stimulus variation is utilized as described in the previous paragraph. The LCMV filter given in equation (9) has a response with nulls or notches at the locations outside $Q_o$ that correspond to sources with significant covariance. Hence, when applied to the mean $m_x$, this filter will also attenuate the mean components of sources located outside $Q_o$ and an accurate estimate of the mean dipole moment in $Q_o$ is obtained, free from contamination by mean components outside $Q_o$. In essence, the covariance component is used to determine source locations and then the source locations are used to design filters for optimal processing of the mean component.

The LCMV filters can also be applied to a single data record x to estimate the net moment present in the volume $Q_o$ at the instant the data record was obtained, i.e., $$m_y(Q_o) = W^T(q_o) x$$

where $w(q_o)$ is given by either equation (9) or equation (12).

In practice the mean vector $m_x$ and covariance matrix $R_x$ are unknown and must be estimated from the measured data. The maximum likelihood estimate of $m_x$ and $R_x$ given M data vectors $x_i$, $i = 1, 2, \ldots, M$, that are independent and identically normally distributed with means $m_x$ and covariance matrix $R_x$ are $$\hat{m}_x = \frac{1}{M} \sum_{i=1}^{M} x_i \quad (14a)$$

$$\hat{R}_x = \frac{1}{M} \sum_{i=1}^{M} (x_i - \hat{m}_x)(x_i - \hat{m}_x)^T. \quad (14b)$$

$\hat{R}_x$ is nonsingular with probability one provided $M > N$. Clearly $\hat{m}_x$ and $\hat{R}_x$ are random quantities. Hence the estimates in equations (13a,b,c) and (10a,b) are also random quantities. Statistical analysis indicates that the variability of the estimates from equations (13a,b,c) and (10a,b) decreases as the ratio M/N increases. As a general guideline, reliable estimates are obtained for $M > 4N$. In other words, the number of sample times M at which data from the N electrodes is taken is preferably at least four times the number N of electrodes.

The LCMV filters may also be used to monitor the neural activity in a specified local region of the brain while attenuating noise and signals due to other regions of the brain. If continuous monitoring is desired, then alternate, continuously updated estimates of the mean and covariance matrix may be utilized to continuously adjust the LCMV filter weights. For example, if an exponential window is used to deemphasize past data, then $$m_x(k) = \lambda m_x(k-1) + (1-\lambda) x(k) \quad (15)$$

$$R_x(k) = \lambda R_x(k-1) + (1-\lambda)[x(k) - m_x(k)][x(k) - m_x(k)]^T \quad (16)$$

where $\lambda < 1$ is the exponential weighting factor, $m_x(k)$ and $R_x$are (k) used to compute the LCMV filter weights at time k and x(k) is the electrode data at time k.

To illustrate the application of the LCMV method, the method may be applied to simulated data as follows. A three spherical shell model of the head is employed with an outer shell radius of 8 cm, middle shell radius of 7.5 cm, and inner shell radius of 6.8 cm. The ratio of skull to soft tissue conductivity is assumed to be 0.0125 and each of the concentric shells is homogeneous within the shell. 125 electrodes are distributed in a known set of locations in an approximately uniform manner over the upper hemisphere of the outer shell.

The data is assumed to be generated by five point sources and contains an additive uncorrelated noise component. Each source is characterized by a data covariance matrix of the form $$R_i = H(q_i) m_i m^T H^T(q_i) \quad (17)$$

where $q_i$ is the source location, and the moment power density for the source is $S(q_i) = m_i m_i^T$. The data covariance matrix $R_x$ is the sum of the individual source covariance matrices and the uncorrelated noise covariance $\sigma^2 I$. The signal to noise ratio (SNR) corresponding to each source is defined as the average power of the source over all electrodes divided by the average noise power $$SNR_i = \frac{tr R_i}{N \sigma^2}. \quad (18)$$

The source locations, moments, and SNR are given in Table 1 below.

The true covariance matrix is used to compute the moment power estimates so that the basic performance characteristics of the algorithm are not confused with the effects of covariance matrix estimation.

Figure 5:
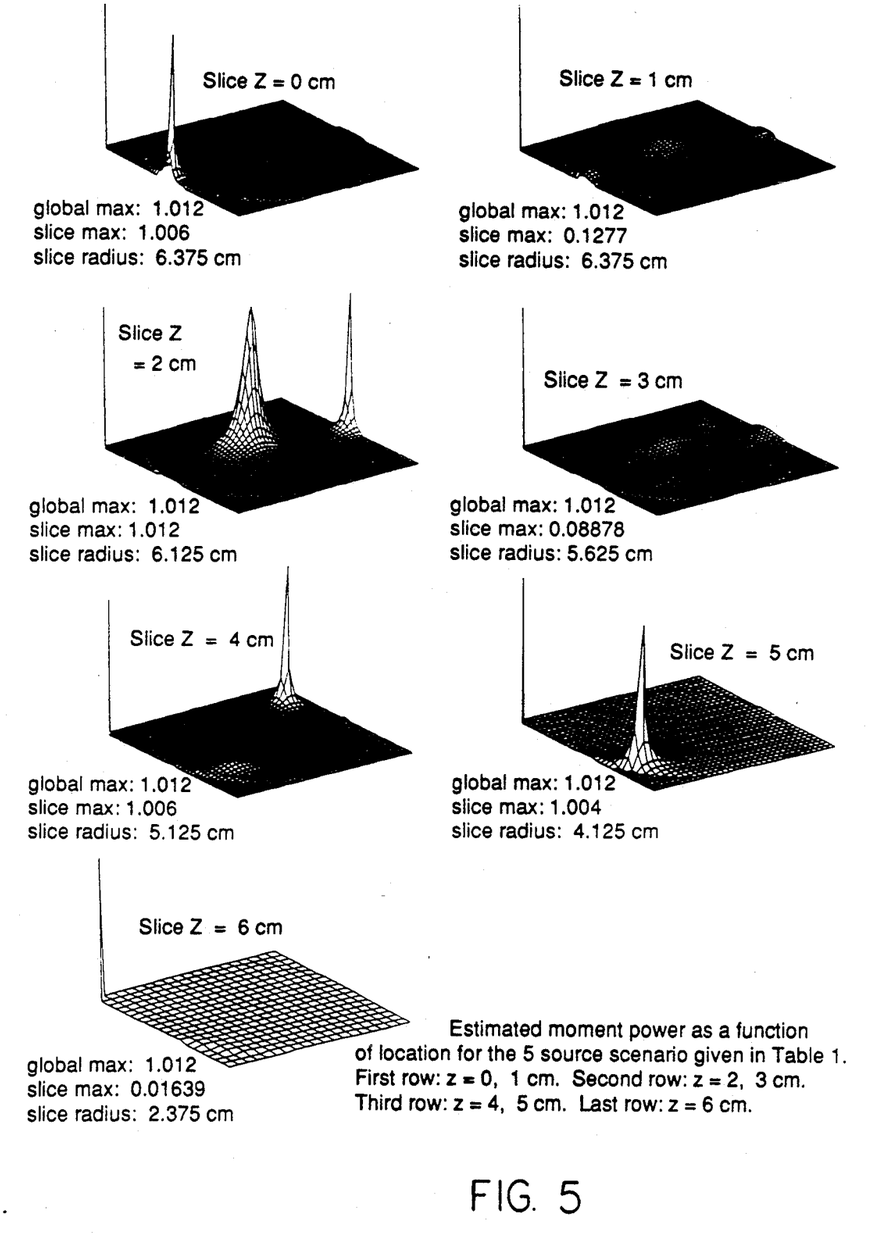
FIG. 5 are illustrative graphs obtained in accordance with the invention on an exemplary model system having five sources.

The results are presented in FIG. 5 as displayed on the display device 21, printed out in hard copy, using an xyz coordinate system where the xy plane separates the upper and lower hemispheres of the brain model. The upper hemisphere is represented by positive values for z. The net moment power $P(Q_o)$ is estimated as a function of x and y for slices of constant z and presented as a three dimensional surface plot. The slices of constant z are spaced by 1 cm (z=0,1,2,3,4,5, and 6 cm). Within each slice, $P(Q_o)$ is estimated on a grid of points spaced by 0.25 cm. Note that as the value of z increases, the radius of the brain in each xy plane decreases. Thus, since the printed size of each slice is the same, the scale along the xy axes varies from slice to slice. However, the grid line spacing is fixed at 0.25 cm. The plotting software required a rectangular grid of points so the circular region in each slice representing the brain is inscribed within a square of length and width equal to the brain diameter for the slice. Lastly, the spike in the upper left corner of each slice is a scaling device: its height represents the maximum (estimated) value of $P(Q_o)$ over all slices.

FIG. 5 illustrates the performance obtained for the source scenario described in Table 1 below. Note that the power associated with each source is the same, $m_i^T m_i = 1$, but the individual SNR's vary. This is because the sources experience differing degrees of attenuation depending on their depth relative to the electrode locations. The attenuation for each source and hence the SNR is determined by $H(q_i)$.

Peaks in the estimated moment power density are evident at all five source locations. The estimated values at the peaks are all between 1 and 1.013, almost exactly equal to the true values of 1.

Simulations have also been conducted to assess performance in the presence of spatially distributed sources and when the actual and assumed parameters of the head model differ. Spatially distributed sources are accurately identified within the limits of the algorithm's resolving capability. Performance degrades gracefully in response to variations between the actual and assumed parameters of the head model. Errors in the assumed conductivity ratio, shell thicknesses, and electrode positions generally result in smeared peaks (corresponding to point sources) and reduced peak amplitudes. The peak amplitudes are reduced because the linear constraint does not guarantee unit gain if the actual and assumed $H(q_o)$ differ and thus the power minimization step leads to cancellation of a portion of the desired source energy.

TABLE 1

| | Source scenario for FIG. 5. | | | | | | |
|---|---|---|---|---|---|---|---|
| Source i | $(q_i)_x$ | $(q_i)_y$ | $(q_i)_z$ | $(m_i)_x$ | $(m_i)_y$ | $(m_i)_z$ | $SNR_i$ |
| 1 | 3.875 | 3.12 | 4 | .7 | .6 | .387 | 21.1 |
| 2 | 6.125 | .125 | 2 | 1 | 0 | 0 | 20.6 |
| 3 | .125 | 1.125 | 2 | 0 | .6 | .8 | 10.7 |
| 4 | −6.125 | .375 | 0 | −1 | 0 | 0 | 15.4 |
| 5 | −3.125 | −1.875 | 5 | −.8 | 0 | .6 | 20.1 |

Figure 2:
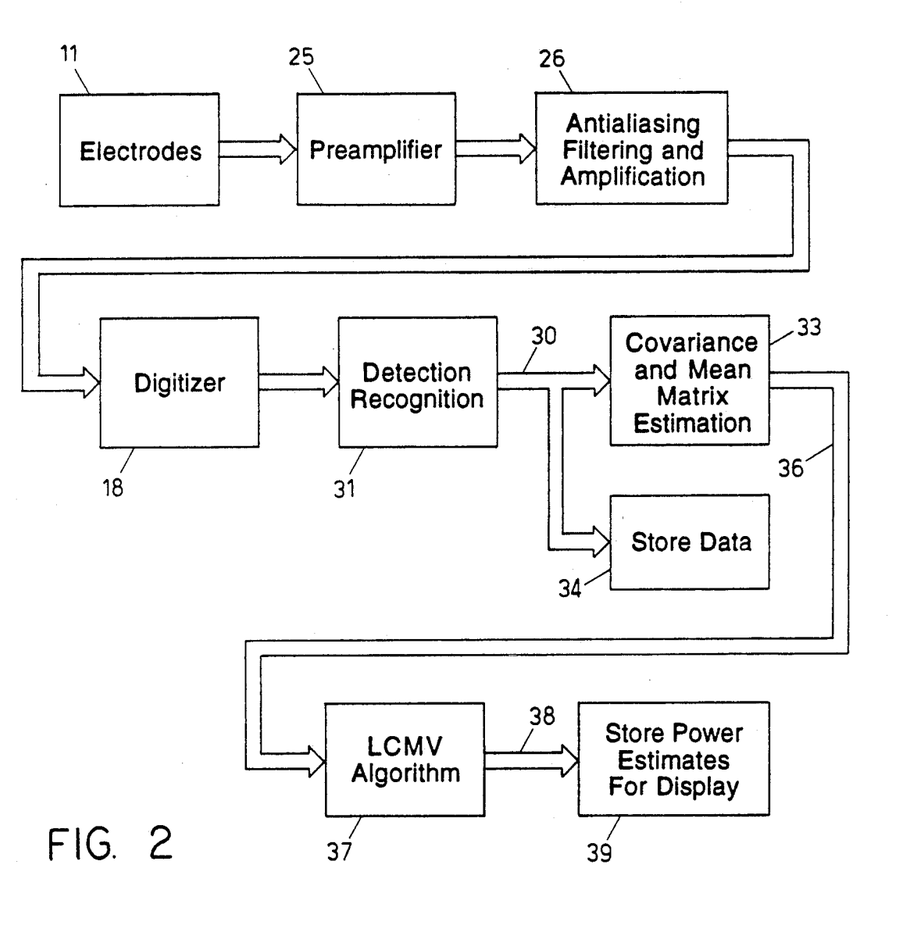
FIG. 2 is an overall block diagram of the functional blocks of the apparatus of the present invention.

A block diagram illustrating the major functional blocks of the apparatus in accordance with the present invention is shown in FIG. 2. Electrodes 11 provide their signals to a preamplifier 25 which provides its output to anti-aliasing filters and amplifiers 25 and 26 within the signal conditioning unit 17. The preamplifiers and the anti-aliasing filters and amplifiers within the blocks 25 and 26 are entirely standard components conventionally utilized in EEG systems, and various suitable components are commercially available. The output of the section 26 is provided to the analog-to-digital converter 18 wherein the conditioned multiple analog signals from the electrodes are converted to digital data on output lines 30. This output is provided to the processing unit 19 which carries out the remaining steps shown in the blocks of FIG. 2. These blocks include an optional detection recognition algorithm 31 which may be utilized to reject artifacts or to detect events of interest for localization processing in the signal data. The output data from the detection algorithm 31, or the direct data on the lines 30 where the detection process 31 is not used, are provided to a covariance matrix estimation 33, which may include mean estimation. Optionally, the data may be provided to a data storage procedure 34 which stores the data, either within the internal memory of the processing unit 19 or in the archival storage device 20 for later retrieval. The output of the covariance matrix and mean estimation process 33 is provided on an output path 36 to the linearly contrained minimum variance (LCMV) process 37. The process 37 provides the power location estimates on an output path 38, and these may be stored for display at 39 or sent immediately to the display device 21.

Assuming that N electrodes are used, there will be N electrode channels sampled by the analog-to-digital conversion step 18. The output of the analog-to-digital conversion 18 at a time incident k can be represented by a N by 1 vector of potentials $X_k$. If one assumes that a number M (greater than N) data vectors $X_j$, where j=1,2, ... N, are available, a variety of covariance or mean matrix estimates can be used in the step 33. A preferred covariance matrix estimator $\hat{R}_x$ for a zero mean case is the following:

$$\hat{R}_x = \frac{1}{M} \sum_{j=1}^{M} x_j x_j^T \quad (19)$$

The estimators of equations (14a) and (14b) may be used for the non-zero mean case.

The $T$ denotes the matrix (or vector) transpose operation. The estimate $R_x$ is an N by N matrix. It should be noted that covariance matrix estimates are only meaningful if the $x_j$ are samples of a stationary random process.

The LCMV algorithm process at 37 estimates the level of neural activity as a function of location within the brain, and thus generates samples of a three dimensional function. The storage of the output of the LCMV algorithm at 39 allows the results to be reviewed by an operator later.

The LCMV algorithm requires a model for the potential at each electrode due to each component of the moment of a dipolar source as a function of source location. This model can be represented as a set of N by 3 matrices $H_i$ where i denotes the ith location within the brain. The first column of $H_i$ is the potential of the N electrodes due to a dipole at location i having unity x, zero y and zero z component dipole movement, assuming an xyz coordinate system. The second column of $H_i$ is the potential at the N electrodes due to a dipole at location i having zero x, unity y and zero z component dipole movement. The third column of $H_i$ is the potential at the N electrodes due to a dipole at location i having zero x, zero y and unity z component dipole moment. These potentials are computed for the xyz reference used in the data collection. The creation of the reference is illustrated with respect to the block diagram in FIG. 3.

Initially, computation of the potential at an electrode requires knowledge of the electrode location. Thus, the first step in the model generation is the measurement of the electrode locations as indicated by the block 45 in FIG. 3. A device such as the Polhemus 3-space digitizer can be used to measure electrode locations. The LCMV algorithm estimates the neural activity at distinct locations (points) in the brain. An "H" is required for each location of interest. Hence, each location must be defined so that the corresponding H is computed. This step is illustrated by the block 46 in FIG. 3. A dense three space dimensional grid of locations allows a three dimensional image of neural activity to be provided.

Figure 3:
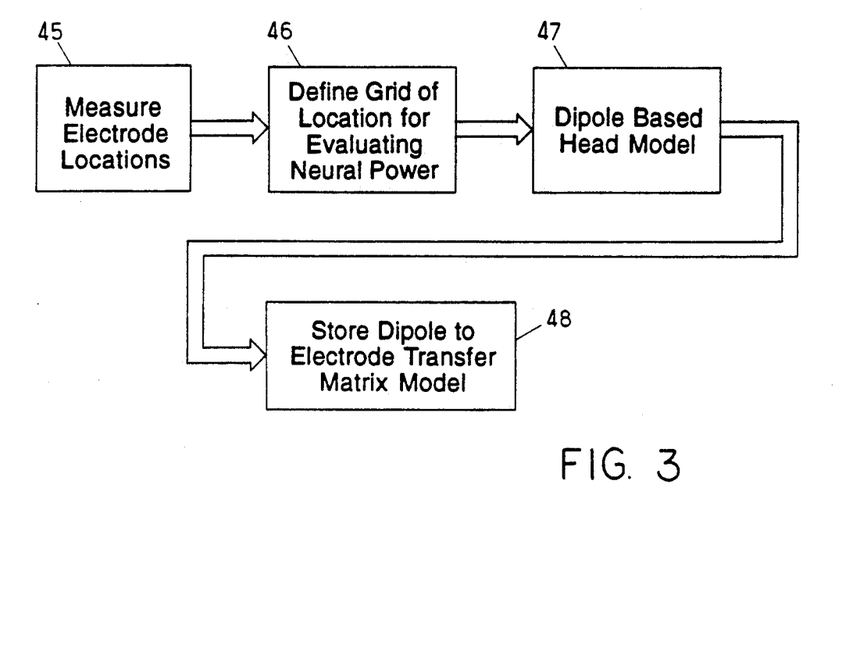
FIG. 3 is a block diagram illustrating the steps carried out in the present invention for the dipole to electrode transfer matrix model generation.

Computation of the electrode potentials due to elemental dipole sources requires a model for the geometry and physiology of the head. This is known as the "forward" problem and is illustrated by the step 47 in FIG. 3. Many different models can be used. For example, a simple and workable approach is to approximate the brain, skull and scalp as three concentric shells with different conductivities. In this case, the jth row of each $H_i$ is obtained from the following equations:

x component:
$$H_{ix} = \quad (20)$$

$$\frac{1}{4\pi SR^2} \sum_{n=1}^{\infty} \frac{X(2n+1)^3}{d_n(n+1)n} b^{n-1}[nR_y P_n(\cos\alpha) + T_x P_n'(\cos\alpha)]$$

y component:

$$H_{iy} = \frac{1}{4\pi SR^2} \sum_{n=1}^{\infty} \frac{X(2n+1)^3}{d_n(n+1)n} b^{n-1}[nR_x P_n(\cos\alpha) + T_y P_n'(\cos\alpha)] \quad (21)$$

z component:

$$H_{iz} = \frac{1}{4\pi SR^2} \sum_{n=1}^{\infty} \frac{X(2n+1)^3}{d_n(n+1)n} b^{n-1}[nR_z P_n(\cos\alpha) + T_z P_n'(\cos\alpha)] \quad (22)$$

In the above equations:
R = outer radius of head,
S = soft tissue conductivity,
X = (skull conductivity)/S, $$d_n = [(n+1)X + n]\left[\frac{nX}{n+1} + 1\right] + \quad (23)$$

$$(1-x)[(n+1)X + n](f_1^{n_1} - f_2^{n_1}) - n(1-X)^2(f_1/f_2)^{n_1}$$

where
$n_1 = 2n+1$,
$f_1 = $ (radius of inner shell)/R,
$f_2 = $ (radius of middle shell)/R;
$P_n(°) = $ Legendre polynomial,
$P_n'(°) = $ associated Legendre polynomial,
$R_1 = [X_1 \; Y_1 \; Z_1]^T$ is dipole location,
$R_2 = [X_2 \; Y_2 \; Z_2]^T$ is jth electrode location,
$R_x = X_1/(R_1^T R_1)^{\frac{1}{2}}$,
$R_y = Y_1/(R_1^T R_1)^{\frac{1}{2}}$,
$R_z = X_1/(R_1^T R_1)^{\frac{1}{2}}$,
$\cos \alpha = R_1^T R_2/[R_1^T R_1 \; R_2^T R_2]^{\frac{1}{2}}$,
$b = (R_1^T R_1)^{\frac{1}{2}}/R$,
and
$T_x = t_x/(t^T t)^{\frac{1}{2}}$,
$T_y = t_y/(t^T t)^{\frac{1}{2}}$,
$T_x = t_x/(t^T t)^{\frac{1}{2}}$
where $$t = [t_x \; t_y \; t_z]^T$$
$$= R_2(R_1^T R_1) - R_1(R_1^T R_2).$$

In practice, the infinite sums in the equations for $H_{ix}$, $H_{iy}$, and $H_{ix}$ are approximated by finite sums. For a further description of the foregoing procedure, see Y. Salu, et al., "An Improved Method For Localizing Electric Brain Dipoles," IEEE Trans. Biomed. Eng., Vol. 37, July 1990, pp. 699–705.

After the $H_i$ have been calculated, these may then be stored for use by the LCMV algorithm, as indicated by the block 48 in FIG. 3.

Figure 4:
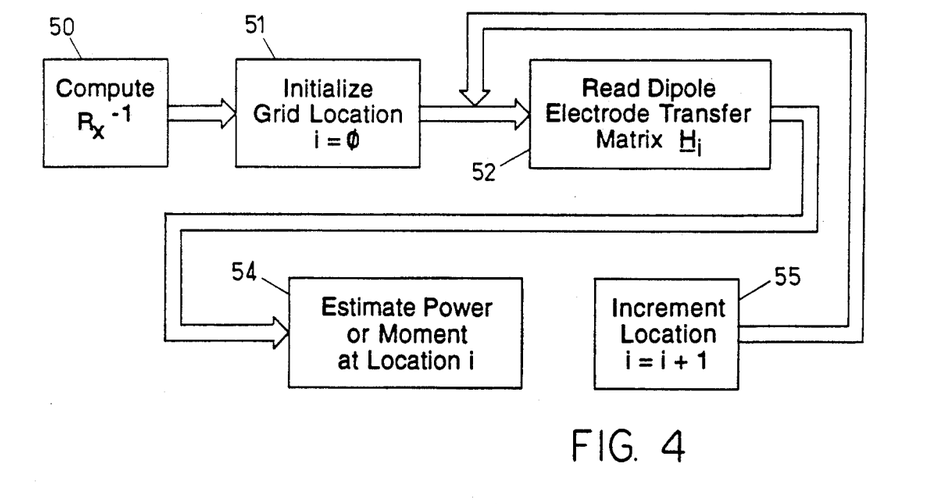
FIG. 4 is a block diagram illustrating the steps in the LCMV algorithm in accordance with the present invention.

The operation of the LCMV algorithm within the processing unit 19 is illustrated in FIG. 4. The fundamental principle of the LCMV method is to provide a spatial filter that passes the neural activity for a specified location while rejecting neural activity at other locations. The power at the output of such a filter is an estimate of the neural activity level for the corresponding locations. The linear constraints (based on $H_i$) ensure that the desired neural signals are passed by the filter with unit gain. Variance minimization (filter output power) eliminates contributions to the filter output of neural sources at locations other than the one of interest.

If x is the vector of electrode potentials, then the filter output $y_i$ for location i is defined in terms of the N by 3 matrix $W_i$ as $y_i = W_i^T x$. The output power (estimate of neural activity level) is the expected value of $y_i^T y_i$. The filter $W_i$ is chosen to minimize the expected value of $y_i^T y_i$ subject to the constraint $H_i^T W = I$. This problem has the solution (e.g., for the zero mean case): $W_i = R_x^{-1} H_i (H_i^T R_x^{-1} H_i)^{-1}$. $R_x$ is the estimate of the data covariance matrix.

Referring to FIG. 4, the first step in the LCMV algorithm is the computation of the matrix $R_x^{-1}$ at 50. The estimate for each location involves this matrix, so it is computed once at the beginning of the algorithm. The process then proceeds at 51 to initialize the grid locations, starting at the first location where $i=0$. The $H_i$ previously computed is read at 52. Then, at 54, the solution for $W_i$ is substituted to find the neural power $P_i$ at location i which is estimated in accordance with $P_i = tr[H_i)^{-1}]$. In this expression, tr denotes the matrix trace operation. The process then proceeds to block 55 at which the location i is incremented in accordance with $i = i+1$, and the process turns to block 52 to read the dipole to electrode transform matrix $H_i$. This process is continued until all of the grid locations are read and the power at each location is estimated.

It is understood that the invention is not limited to the particular embodiments described herein, but embraces such modified forms thereof as come within the scope of the following claims.

What is claimed is:

1. A method of determining the location of sources of electrical activity within the head of an individual, comprising the steps of:
   (a) placing a plurality of electrodes at known positions on the head of an individual;
   (b) obtaining electrical signals from the electrodes indicative of the electrical potentials at the electrodes;
   (c) determining a matrix of source location to electrode potential transfer functions for the electrodes for electrical events at locations within the head of the individual known with respect to the electrodes;
   (d) determining a covariance matrix estimate on the data from the electrodes at a plurality of points in time;
   (e) determining the inverse of the covariance matrix estimate for the data from the electrodes at a plurality of points in time; and
   (f) for at least a plurality of the predetermined locations in the brain, determining the estimated signal power at such locations as a function of the inverse covariance matrix estimate and the source location to electrode transfer functions in a manner which satisfies a linearly constrained minimum variance criterion.

2. The method of claim 1 wherein the sources of potential correspond to dipoles having essentially zero mean, and wherein the covariance matrix $R_x$ is estimated in accordance with the expression:

$$\hat{R}_x = \frac{1}{M} \sum_{j=1}^{M} x_j x_j^T$$

where M is a chosen number of data points which is greater than or equal to the number of electrodes and $x_j$ is the vector of data from the electrodes at a point j in time.

3. The method of claim 2 wherein a spatial filter $W(q_o)$ for each of the locations $q_o$ in a volume $Q_o$ within the head is estimated in accordance with the expression $$W(q_o) = \hat{R}_x^{-1} H(q_o)(H^T(q_o) \hat{R}_x^{-1} H(q_o))^{-1},$$

where $H(q_o)$ is a matrix of the source to electrode transfer functions for the locations $q_o$, and the estimated power $\hat{P}(Q_o)$ is determined in accordance with the expression:

$$\hat{P}(Q_o) = tr\{W^T(q_o) \hat{R}_x W(q_o)\}$$

and tr denotes the trace of the matrix.

4. The method of claim 2 wherein the estimated power $\hat{P}(Q_o)$ at the plural locations $q_o$ within the head, each in a volume $Q_o$, is determined in accordance with the expression $$\hat{P}(Q_o) = tr\{(H^T(q_o)\hat{R}_x^{-1} H(q_o))^{-1}\}$$

where $H(q_o)$ is the matrix of source to electrode transfer functions for the locations $q_o$, and tr denotes the trace of the matrix.

5. The method of claim 3 including the step of determining the estimated dipole moment at each of the locations $q_o$ within a volume $Q_o$ of brain corresponding to the data record $x_j$ in accordance with the expression:

$$m_j(Q_{10}) = W^T(q_o) X_j.$$

6. The method of claim 1 including the step of displaying the estimated power at the predetermined locations to a user.

7. The method of claim 1 wherein the predetermined locations are points in a three-dimensional rectangular grid which covers the volume within the head.

8. The method of claim 1 wherein the sources of potential correspond to dipoles having a non-zero mean, and wherein a spatial filter $W(q_o)$ for each of the locations $q_o$ within the head is determined in accordance with the expression:

$$W(q_o) = (\hat{R}_x + mm^T)^{-1} H(q_o) \{H^T(q_o) (\hat{R}_x + mm^T)^{-1} H(q_o)\}^{-1}$$
where
$$m = [I - H(q_o) (H^T(q_o)H(q_o)H(q_o))^{-1} H^T(q_o)]\hat{m}_x,$$

$$\hat{m}_x = \frac{1}{M} \sum_{i=1}^{M} x_i,$$

$$\hat{R}_x = \frac{1}{M} \sum_{i=1}^{M} (x_i - \hat{m}_x)(x_i - \hat{m}_x)^T,$$

$x_i$ is the vector of electrode data at a point in time i, $H(q_o)$ is a matrix of source to electrode potential transfer functions for the electrodes for electrical events for the locations $q_o$.

9. The method of claim 8 wherein the estimated power $\hat{P}(Q_o)$ at each of the locations $q_o$ which is within a volume of brain $Q_o$ is determined in accordance with the expression:

$$\hat{P}(Q_o) = tr\{W^T(q_o)(\hat{R}_x + \hat{m}_x\hat{m}_x^T)W(q_o)\}.$$

where tr denotes the trace of the matrix.

10. The method of claim 8 including the step of determining the estimated dipole moment at each location $q_o$ within a volume of brain $Q_o$ corresponding to a data record $x_j$ in accordance with the expression:

$$m_j(Q_o) = W^T(q_o)x_j.$$

11. The method of claim 1 including the additional step, at or before the step of obtaining electrical signals from the electrodes, of applying a stimulus to the individual which will result in electrical activity within the head of the individual.

12. A method of determining the location of sources of electrical activity within the head of an individual, comprising the steps of:
(a) placing a plurality of electrodes at known positions on the head of an individual;
(b) obtaining electrical signal data from the electrodes indicative of the electrical potentials at the electrodes;
(c) passing the electrode signal data through a filter bank comprising a plurality of narrow band spatial filters wherein each filter substantially passes energy from a location within the brain known with respect to the electrode positions and rejects signal energy from other locations, wherein the filters meet a linearly constrained minimum variance criterion; and
(d) estimating the signal power in the output of each filter, which corresponds to the power at each of the locations.

13. The method of claim 12 including the step of displaying the estimated power at each location.

14. The method of claim 12 wherein the spatial filters $W(q_o)$ for each of the locations $q_o$ within the head are determined in accordance with the expression:

$$W(q_o) = (\hat{R}_x + mm^T)^{-1}H(q_o)\{H^T(q_o)(\hat{R}_x + mm^T)^{-1}H(q_o)\}^{-1}$$
where
$$m = [I - H(q_o)(H^T(q_o)H(q_o)H(q_o))^{-1}H^T(q_o)]\hat{m}_x,$$

$$\hat{m}_x = \frac{1}{M}\sum_{i=1}^{M} x_i,$$

$$\hat{R}_x = \frac{1}{M}\sum_{i=1}^{M}(x_i - \hat{m}_x)(x_i - \hat{m}_x)^T,$$

$x_i$ is the vector of electrode data at a point in time i,
$H(q_o)$ is a matrix of source to electrode potential transfer functions for the electrodes for electrical events for the locations $q_o$.

15. The method of claim 14 wherein the estimated power at least of the locations $q_o$ which is within a volume of brain $Q_o$ is determined in accordance with the expression:

$$P(Q_o) = tr\{W^T(q_o)(\hat{R}_x + \hat{m}_x\hat{m}_x^T)W(q_o)\}.$$

where tr denotes the trace of the matrix.

16. The method of claim 14 including the step of determining the estimated dipole moment at each location $q_o$ within a volume of brain $Q_o$ corresponding to a data record $x_j$ in accordance with the expression:

$$m_j(Q_o) = W^T(q_o)x_j.$$

17. The method of claim 12 wherein the sources of potential correspond to dipoles having essentially zero mean, and wherein the estimated power $\hat{P}_{(Q_o)}$ at the plural locations $q_o$ within the head, each in a volume $Q_o$, is determined in accordance with the expression $$\hat{P}(Q_o) = tr\{(H^T(q_o)\hat{R}_x^{-1}H(q_o))^{-1}\}$$

where $H(q_o)$ is the matrix of source to electrode transfer functions for the locations $q_o$, tr denotes the trace of the matrix, and $\hat{R}_x$ is estimated in accordance with the expression:

$$\hat{R}_x = \frac{1}{M}\sum_{j=1}^{M} x_j x_j^T$$

where M is a chosen number of data points which is greater than or equal to the number of electrodes and $X_j$ is the vector of data from the electrodes at a point j in time.

18. The method of claim 12 including the additional step, at or before the step of obtaining electrical signals from the electrodes, of applying a stimulus to the individual which will result in electrical activity within the head of the individual.

19. A method of determining the location of sources of electrical activity within the head of an individual, comprising the steps of:
(a) placing a plurality of electrodes at known positions on the head of an individual;
(b) obtaining electrical signal data from the electrodes indicative of the electrical potentials at the electrodes;
(c) passing the electrode signal data through a filter bank comprising a plurality of narrow band spatial filters wherein each filter substantially passes signal energy from a location within the brain known with respect to the electrode positions and rejects signal energy from other locations, wherein the filters meet a signal linearly constrained minimum variance criterion; and
(d) estimating the dipole moment in the output of each filter, which corresponds to the dipole moment at each of the locations.

20. The method of claim 19 including the step of displaying the dipole moments at each location.

21. The method of claim 19 wherein the spatial filters $W(q_o)$ for each of the locations $q_o$ within the head are determined in accordance with the expression:

$$W(q_o) = (\hat{R}_x + mm^T)^{-1}H(q_o)\{H^T(q_o)(\hat{R}_x + mm^T)^{-1}H(q_o)\}^{-1}$$
where
$$m = [I - H(q_o)(H^T(q_o)H(q_o)H(q_o))^{-1}H^T(q_o)]\hat{m}_x,$$

$$\hat{m}_x = \frac{1}{M}\sum_{i=1}^{M} x_i,$$

$$\hat{R}_x = \frac{1}{M}\sum_{i=1}^{M}(x_i - \hat{m}_x)(x_i - \hat{m}_x)^T,$$

$x_i$ is the vector of electrode data at a point in time i,
$H(q_o)$ is a matrix of source to electrode potential transfer functions for the electrodes for electrical events for the locations $q_o$.

22. The method of claim 21 including the step of determining the estimated power at each of the locations $q_o$ which is within a volume of brain $Q_o$ in accordance with the expression:

$$\hat{P}(Q_o) = tr\{W^T(q_o)(\hat{R}_x + \hat{m}_x\hat{m}_x^T)W(q_o)\}.$$

where tr denotes the trace of the matrix.

23. The method of claim 21 wherein the estimated moment at each of the locations $q_o$ within a volume of brain $Q_o$ corresponding to a data record $x_j$ in accordance with the expression:

$$m_j(Q_o) = W^T(q_o)x_j.$$

24. The method of claim 19 wherein the sources of potential correspond to dipoles having essentially zero mean, and including the step of determining the estimated power $\hat{P}(Q_o)$ at the plural locations $q_o$ within the head, each in a volume $Q_o$, in accordance with the expression $$\hat{P}(Q_o) = tr\{(H^T(q_o)\hat{R}_x^{-1}H(q_o))^{-1}\}$$

where $H(q_o)$ is the matrix of source to electrode transfer functions for the locations $q_o$, tr denotes the trace of the matrix, and $\hat{R}_x$ is estimated in accordance with the expression:

$$\hat{R}_x = \frac{1}{M} \sum_{j=1}^{M} x_j x_j^T$$

where M is a chosen number of data points which is greater than or equal to the number of electrodes and $x_j$ is the vector of data from the electrodes at a point j in time.

25. The method of claim 19 including the additional step, at or before the step of obtaining electrical signals from the electrodes, of applying a stimulus to the individual which will result in electrical activity within the head of the individual.

26. Apparatus for localization of intracerebral sources of electrical activity, comprising:
 (a) a plurality of electrodes adapted to be placed on the head of an individual at known positions;
 (b) a digitizer converting analog signals from the electrodes to digital data signals;
 (c) processing means for processing the digital data signals including (1) a plurality of narrow band spatial filters, each filter substantially passing signal energy from a location within the brain known with respect to the electrode positions and rejecting signal energy from other locations, wherein the filters meet a linearly constrained minimum variance criterion, and (2) means for estimating the signal power in the output of each filter, which corresponds to the power at each of the locations.

27. The apparatus of claim 26 including a display device connected to the processing means to display the estimated power at each location.

28. The apparatus of claim 26 wherein the spatial filters $W(q_o)$ for each of the locations $q_o$ within the head are constructed in accordance with the expression:

$$W(q_o) = (\hat{R}_x + mm^T)^{-1}H(q_o)\{H^T(q_o)(\hat{R}_x + mm^T)^{-1}H(q_o)\}^{-1}$$
where
$$m = [I - H(q_o)(H^T(q_o)H(q_o)H(q_o))^{-1}H^T(q_o)]\hat{m}_x,$$

$x_i$ is the vector of electrode data at a point in time i, $$\hat{m}_x = \frac{1}{M} \sum_{i=1}^{M} x_i,$$

$$\hat{R}_x = \frac{1}{M} \sum_{i=1}^{M} (x_i - \hat{m}_x)(x_i - \hat{m}_x)^T,$$

$H(q_o)$ is a matrix of source to electrode potential transfer functions for the electrodes for electrical events for the locations $q_o$.

29. The apparatus of claim 28 wherein the processing means estimates the signal power at each of the locations $q_o$ which is within a volume of brain $Q_o$ in accordance with the expression:

$$\hat{P}(Q_o) = tr\{W^T(q_o)(\hat{R}_x + \hat{m}_x\hat{m}_x^T)W(q_o)\}.$$

where tr denotes the trace of the matrix.

30. The apparatus of claim 28 wherein the processing means further estimates the moment at each of the locations $q_o$ within a volume of brain $Q_o$ corresponding to a data record $x_j$ in accordance with the expression:

$$m_j(Q_o) = W^T(q_o)x_j.$$

31. The apparatus of claim 26 further including a stimulator for applying a stimulus to an individual which will result in electrical activity within the head of the individual.

32. Apparatus for localization of intracerebral sources of electrical activity, comprising:
 (a) a plurality of electrodes adapted to be placed on the head of an individual at known positions;
 (b) a digitizer converting analog signals from the electrodes to digital data signals;
 (c) processing means for processing the digital data signals including (1) a plurality of narrow band spatial filters, each filter substantially passing signal energy from a location within the brain known with respect to the electrode positions and rejecting signal energy from other locations, wherein the filters meet a linearly constrained minimum variance criterion, and (2) means for estimating the signal power in the output of each filter, which corresponds to the dipole moment at each of the locations.

33. The apparatus of claim 32 including a display device connected to the processing means to display the estimated moment at each location.

34. The apparatus of claim 32 wherein the spatial filters $W(q_o)$ for each of the locations $q_o$ within the head are determined in accordance with the expression:

$$W(q_o) = (\hat{R}_x + mm^T)^{-1}H(q_o)\{H^T(q_o)(\hat{R}_x + mm^T)^{-1}H(q_o)\}^{-1}$$
where
$$m = [I - H(q_o)(H^T(q_o)H(q_o))^{-1}H^T(q_o)]\hat{m}_x,$$

$$\hat{m}_x = \frac{1}{M} \sum_{i=1}^{M} x_i,$$

$$\hat{R}_x = \frac{1}{M} \sum_{i=1}^{M} (x_i - \hat{m}_x)(x_i - \hat{m}_x)^T,$$

$x_i$ is the vector of electrode data at a point in time i,
$H(q_o)$ is a matrix of source to electrode potential transfer functions for the electrodes for electrical events for the locations $q_o$.

35. The apparatus of claim 34 wherein the processing means estimates the signal power at each of the locations $q_o$ which is within a volume of brain $Q_o$ in accordance with the expression:

$$\hat{P}(Q_o) = tr\{W^T(q_o)(\hat{R}_x + \hat{m}_x\hat{m}_x^T)W(q_o)\}.$$

where tr denotes the trace of the matrix.

36. The apparatus of claim 34 wherein the processing means determines the estimated moment at each of the locations $q_o$ within a volume of brain $Q_o$ corresponding to a data record $x_j$ in accordance with the expression:

$$m_j(Q_o) = W^T(q_o)x_j.$$

* * * * *

UNITED STATES PATENT AND TRADEMARK OFFICE
CERTIFICATE OF CORRECTION

PATENT NO. : 5,263,488
DATED : November 23, 1993
INVENTOR(S) : Van Veen, et al.

It is certified that error appears in the above-indentified patent and that said Letters Patent is hereby corrected as shown below:

In column 5, line 20 of the patent, delete "having".

In column 6, line 11 of the patent, "w($q_0$)" should be --W($q_0$)--.

In column 6, line 13 (equation 4a) of the patent, "$m_y = W^T(q_o)_{mx}$" should be --$m_y = W^T(q_o) m_x$--.

In column 6, line 21 (equation 5a) of the patent, "$q \epsilon Q$" should be --$q \epsilon Q_o$--.

In column 6, line 25 (equation 5b) of the patent, "$q \epsilon Q$" should be --$q \epsilon Q_o$--.

In column 6, line 26 (equation 5b) of the patent, "$q \notin Q$" should be --$q \notin Q_o$--.

In column 7, line 5 of the patent, "Substation" should be --substitution--.

In column 7, line 21 (equation 11) of the patent, all occurrences of "(q0)" should be --($q_0$)--.

In column 7, line 29 of the patent, "(ii)," should be --(11)--.

In column 7, line 49 (equation 13c) of the patent, "$\hat{P}(Q_0) = tr\{W^T(q_0)(R_x + m_x m_x^T) W(q_0)\}.tm(13c)$" should be --$\hat{P}(Q_0) = tr\{W^T(q_0)(R_x + m_x m_x^T) W(q_0)\}.$ (13c)--.

UNITED STATES PATENT AND TRADEMARK OFFICE
CERTIFICATE OF CORRECTION

PATENT NO.  : 5,263,488
DATED       : November 23, 1993
INVENTOR(S) : Van Veen, et al.

It is certified that error appears in the above-indentified patent and that said Letters Patent is hereby corrected as shown below:

In column 8, line 25 of the patent, "$w(q_0)$" should be --$W(q_0)$--.

In column 8, line 67 of the patent, "$R_x are(k)$" should be --$R_x(k)$ are--.

In column 9, line 16 (equation 17) of the patent, "$R_i = H(q_i) m_i m^T H^T(q_i)$" should be --$R_i = H(q_i) m_i m_i^T H^T(q_i)$--.

In column 12, line 30 of the patent, "$R_z = X_1/(R_1^T R_1)^{\frac{1}{2}},$" should be --$R_z = Z_1/(R_1^T R_1)^{\frac{1}{2}},$--.

In column 12, line 36 of the patent, "$T_x = t_x/(t^T t)^{\frac{1}{2}}$" should be --$T_z = t_z/(t^T t)^{\frac{1}{2}}$--.

In column 12, line 44 of the patent, "$H_{ix}$" should be --$H_{iz}$--.

In column 13, line 15 of the patent, "$P_i = tr[H_i)^{-1}].$" should be --$P_i = tr[H_i^T R_x^{-1} H_i)^{-1}].$--.

In column 14, line 9 of the patent, "$)q_0)$" should be --$(q_0)$--.

In column 14, line 16 of the patent, "$\hat{P}(Q_0) = tr\{(H^T(_{q_0}) \hat{R}_x^{-1} H(_{q_0}))^{-1}\}$" should be --$\hat{P}(Q_0) = tr\{(H^T(q_0) R_x^{-1} H(q_0))^{-1}\}$--.

In column 14, line 27 of the patent, "$m_j(Q_{10}) = W^T(q_0) X_j.$" should be --$m_j(Q_0) = W^T(q_0) X_j.$--.

Page 2 of 3

UNITED STATES PATENT AND TRADEMARK OFFICE
CERTIFICATE OF CORRECTION

PATENT NO. : 5,263,488
DATED : November 23, 1993
INVENTOR(S) : Van Veen, et al.

It is certified that error appears in the above-indentified patent and that said Letters Patent is hereby corrected as shown below:

In column 15, line 47 of the patent, "least" should be --each--.

In column 17, line 54 of the patent, "$m=[I-H(q_0)(H^T(q_0)H(q_0)H(q_0))^{-1}H^T(q_0)]\hat{m}_x,$" should be --$m=[I-H(q_0)(H^T(q_0)H(q_0))^{-1}H^T(q_0)]\hat{m}_x,$--.

In column 18, line 31 of the patent, "signal power" should be --dipole moment--.

Signed and Sealed this

Twelfth Day of July, 1994

*Attest:*

BRUCE LEHMAN

*Attesting Officer*         *Commissioner of Patents and Trademarks*